US005733322A

United States Patent [19]
Starkebaum

[11] Patent Number: 5,733,322
[45] Date of Patent: Mar. 31, 1998

[54] POSITIVE FIXATION PERCUTANEOUS EPIDURAL NEUROSTIMULATION LEAD

[75] Inventor: Warren L. Starkebaum, Plymouth, Minn.

[73] Assignee: Medtronic, Inc., Minneapolis, Minn.

[21] Appl. No.: 447,376

[22] Filed: May 23, 1995

[51] Int. Cl.[6] ........................................ A61N 1/05
[52] U.S. Cl. ........................................ 607/117
[58] Field of Search .................. 607/117, 116, 607/122, 126

[56] References Cited

U.S. PATENT DOCUMENTS

| | | | |
|---|---|---|---|
| 4,044,774 | 8/1977 | Corbin et al. | 128/404 |
| 4,141,365 | 2/1979 | Fischell et al. | 128/404 |
| 4,285,347 | 8/1981 | Hess | 607/117 |
| 4,379,462 | 4/1983 | Borkan et al. | 128/786 |
| 4,414,986 | 11/1983 | Dickhudt et al. | 607/117 |
| 4,538,624 | 9/1985 | Tarjan | 128/784 |
| 4,549,556 | 10/1985 | Tarjan et al. | 128/785 |
| 4,800,898 | 1/1989 | Hess et al. | 607/116 |
| 5,344,439 | 9/1994 | Otten | 607/126 |

FOREIGN PATENT DOCUMENTS 733694  5/1980  U.S.S.R. ................ 607/126

OTHER PUBLICATIONS

"Lumbar Epidural Anatomy", by Q.H. Hogan, M.D., in Anesthesiology, vol. 75, No. 5, Nov. 1991, pp. 767–775.

*Primary Examiner*—Lee S. Cohen
*Attorney, Agent, or Firm*—Curtis D. Kinghorn; Harold R. Patton

[57] ABSTRACT

A neurological epidural lead is disclosed having an extension that extends distally beyond the most distal electrode. The length of the extension corresponds to the length of one ore more vertebral segments. The lead is placed in the epidural space so that the electrodes are positioned as desired. In positioning the electrodes, the extension passes through at least one area where the epidural space between the dura and the spinal canal wall is very narrow because the dura and spinal canal wall are in contact. As a result, the extension is held in place by contact with both the dura and spinal canal wall so that lateral lead migration of the electrodes is minimized.

32 Claims, 7 Drawing Sheets

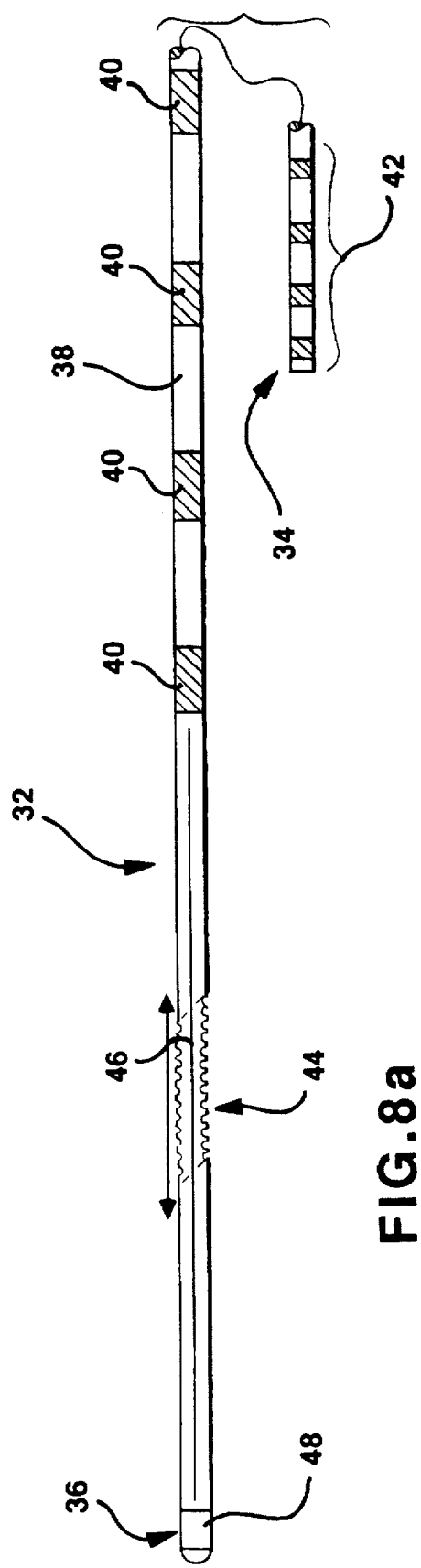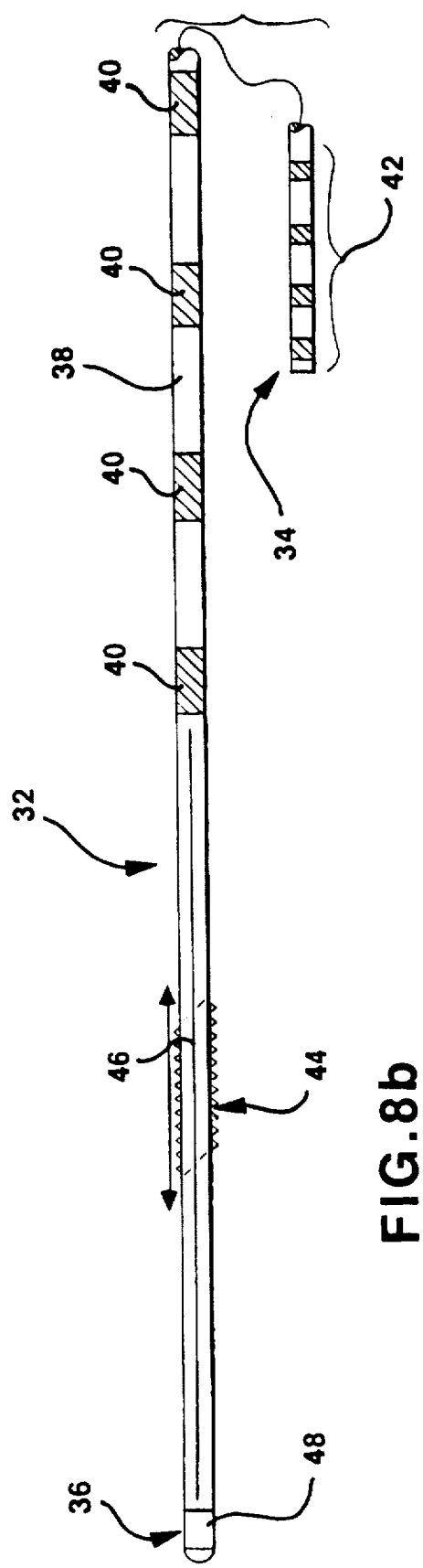

POSITIVE FIXATION PERCUTANEOUS EPIDURAL NEUROSTIMULATION LEAD

BACKGROUND OF THE INVENTION

1. Field of the Invention

The invention relates to a lead for electrically stimulating a patient's neuraxis and more particularly to an apparatus and method for fixing such a lead in the epidural space of a spinal column to prevent lateral lead migration.

2. Description of Related Art

Applying electrical fields to a spinal column has been found to be an effective way to treat pain in many patients with chronic pain. The electrical field is produced by a lead such as is shown in FIG. 1 generally labeled 2. Lead 2 has a proximal end 4 and a distal end 6. Distal end 6 has at least two electrodes 8. An implantable pulse generator (IPG) 10 is attached to proximal end 4. Electrodes 8 are connected to IPG 10 by wires extending through lead 2 from electrodes 8 to proximal end 4. Distal end 6 is placed near the spinal column 12. An electrical potential is applied between pairs of the electrodes 8. The resulting electrode field penetrates the dorsal column of the spinal column 12 and causes parasthesia in the patient. The parasthesia blocks the transmission of the pain impulses up the spinal cord to the brain.

In many applications, as shown in FIGS. 2 through 4, lead 2 is inserted percutaneously through a needle into the epidural space 14 formed between the dura 16 of the spinal column 12 and the spinal canal wall 18. In passing into the epidural space 14, the lead 2 passes through a small hole 20 formed in ligamentum flavum 22 by the needle. Once, lead 2 is introduced into the epidural space 14, lead 2 is moved up through epidural space 14 to the desired location. Because the ligamentum flavum 22 is a fairly tough durable material, lead 2 cannot move laterally, that is, transverse to the axis of lead 2, where lead 2 passes through the ligamentum flavum 22. However, lead 2 may move axially. To prevent this, a stop 24 is placed along lead 2 outside spinal column 12 near the point where lead 2 passes into ligamentum flavum 22. Stop 24 is sutured to surrounding tissue 26 to prevent lead 2 from moving axially.

As described above, lead 2 in the epidural space 14 is prevented from moving axially by the attachment of stop 24 to the tissue 26 outside the spinal column 12, and laterally near where lead 2 passes through the ligamentum flavum 22. However, as shown in FIG. 3, distal end 6 is not securely anchored in the epidural space 14. Consequently distal end 6 may move laterally in the epidural space 14. It is believed that this lateral migration of the distal end 6 of lead 2 occurs fairly regularly. This causes a problem in that even a slight movement of electrodes 8 laterally, for example one to two millimeters, can produce a significant change in the amount and location of parasthesia induced by lead 2. In fact, it is believed that this lateral migration of the distal end 6 of lead 2 is the primary cause of therapy deterioration in patients with implanted neurological epidural leads. Studies have shown that in up to 25 percent of the cases where neurological epidural leads have been implanted and were initially effective, the leads needed to be surgically removed later because of therapeutic deterioration or failure. It is believe that lateral lead migration is the primary cause of these deterioration and failures.

To solve the problem of lateral lead migration of the electrodes 8 at distal end 6, protruding structure has been added to the distal end 6 of lead 2. This protruding structure causes distal end 6 to "stick" or be "anchored" into the tissue around distal end 6 to prevent distal end 6 from moving laterally. Because distal end 6 cannot move laterally, electrodes 8 are prevented from moving laterally. An example of this type of lead anchoring system is disclosed in U.S. Pat. No. 5,344,439 issued to Lynn Otten on Sep. 6, 1994.

However, the lead anchoring systems that rely on protruding structures at the distal end 6 of lead 2 suffer from a drawback related to the physiology of the spinal column 12. Recent research has revealed that the epidural space 14 is not merely the flattened space between the dura 16 and the spinal canal wall 18. *Lumbar Epidural Anatomy, A New Look by Cryomicrotome Section*, Quinn H. Hogan M. D., Anesthesiology 75: 767–775, 1991. Instead, as shown in FIG. 5, the epidural space 14 has a repeating structure along the spinal column 12. Id. Within the vertebra of spinal column 12, there is a fairly compact space between the dura 16 and the spinal canal wall 18 because dura 16 and spinal canal wall 18 are in contact with each other. Between the vertebra, the epidural space 14 expands significantly so that there is an increased distance between the dura 16 and the spinal canal wall 18. Consequently, if lead 2 with the protruding anchoring fixtures at the distal end 6, such as is shown in the '439 patent described above, were placed in epidural space 14 where there is a significant distance between the dura 16 and the spinal canal wall 18, there would be insufficient contact between the anchoring protrusions and the dura 16 and spinal canal wall 18 to prevent lead 2 from moving laterally.

U.S. Pat. No. 4,538,624 issued to P. Tarjan on Sep. 3, 1985, and U.S. Pat. No. 4,549,556 issued to Tarjan et al. on Oct. 29, 1985, disclose methods of anchoring neurological epidural leads 2. As disclosed by these patents and as shown in FIGS. 6, an extension 28 extends distally beyond the most distal electrode 8 and terminates in an extension end 30. Lead 2 is introduced percutaneously into the epidural space 14 through a needle as described above. Lead 2 is moved so that electrodes 8 are positioned at the desired location. Extension 28 extends within epidural space 14 distally beyond electrodes 8. Epidural space 14 is accessed near extension end 30. Extension end 30 is retrieved and anchored outside the spinal column 12 (FIG. 7).

The process of retrieving and anchoring extension end 30 is difficult and requires an additional puncture to and resulting opening in the spinal canal wall 18. It is desirable to find a way to anchor distal end 6 easily and without having to puncture the spinal canal wall 18.

SUMMARY OF THE INVENTION

A neurological epidural lead is disclosed having an extension that extends distally beyond the most distal electrode. The length of the extension corresponds to the length of one or more vertebral segments. The lead is placed in the epidural space so that the electrodes are positioned as desired. In positioning the electrodes, the extension passes through at least one area where the epidural space between the dura and the spinal canal wall is very narrow because the dura and spinal canal wall are in contact. As a result, the extension is held in place by contact with both the dura and spinal canal wall so that lateral lead migration of the electrodes is minimized.

It is a primary object of the invention to provide a neurological epidural lead that will not migrate laterally near the electrodes after placement in the epidural space.

It is another object of the invention to provide an anchoring system for preventing lateral movement of the electrodes in a neurological epidural lead that is easy and effective to use.

It is yet another object of the invention to provide a neurological epidural lead that is easy to implant.

It is another object of the invention to provide a neurological epidural lead that is easy to remove.

It is another object of the invention to provide a neurological epidural lead with an anchoring system for preventing lateral movement of the electrodes that is relatively easy to manufacture.

These and other objects of the invention will be clear with reference to the attached drawings and the following detailed description of the invention. Throughout this description, like elements, wherever referred to, are referenced by like reference numbers.

BRIEF DESCRIPTION OF THE DRAWINGS

FIG. 8 is a side elevational view of a neurological epidural lead according to the present invention.

DETAILED DESCRIPTION OF THE INVENTION

Figure 1:
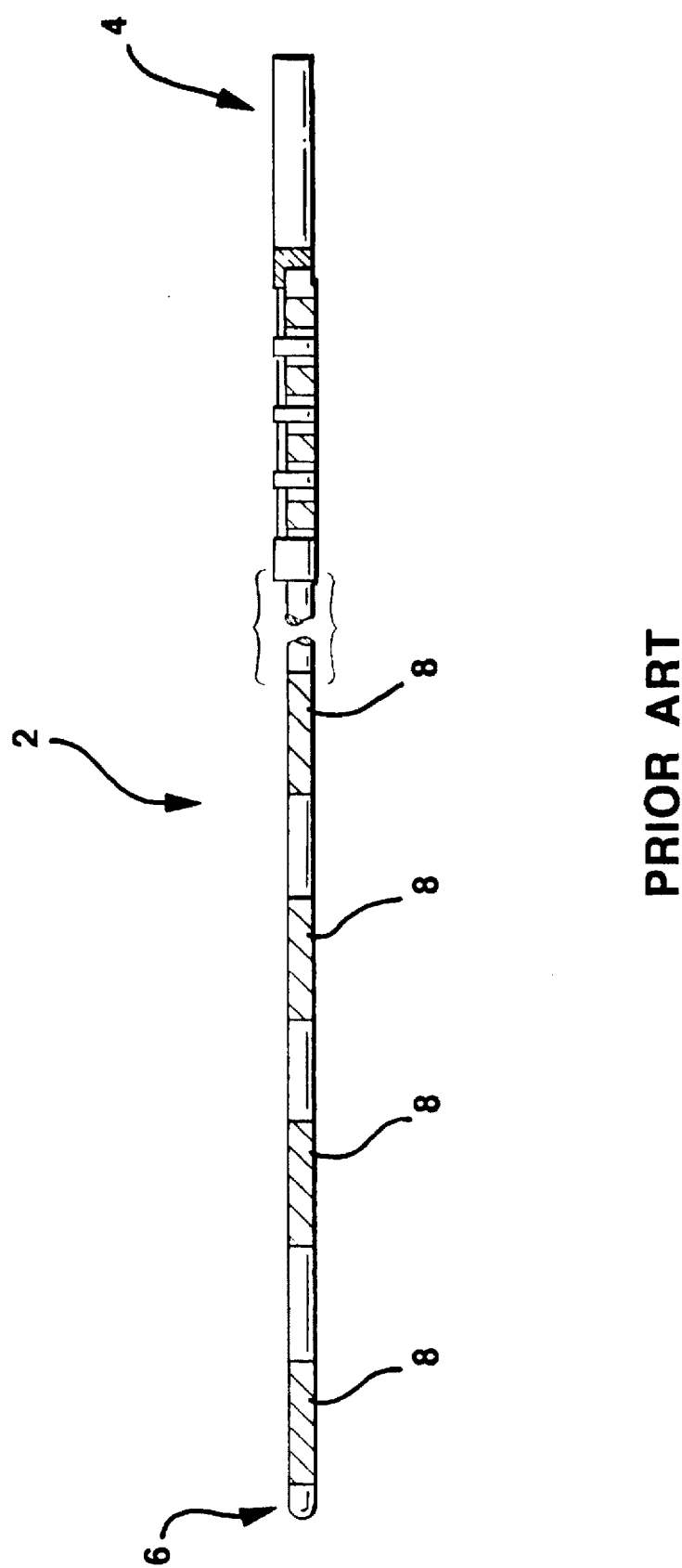
FIG. 1 is a perspective view of a prior art neurological epidural lead.
Figure 2:
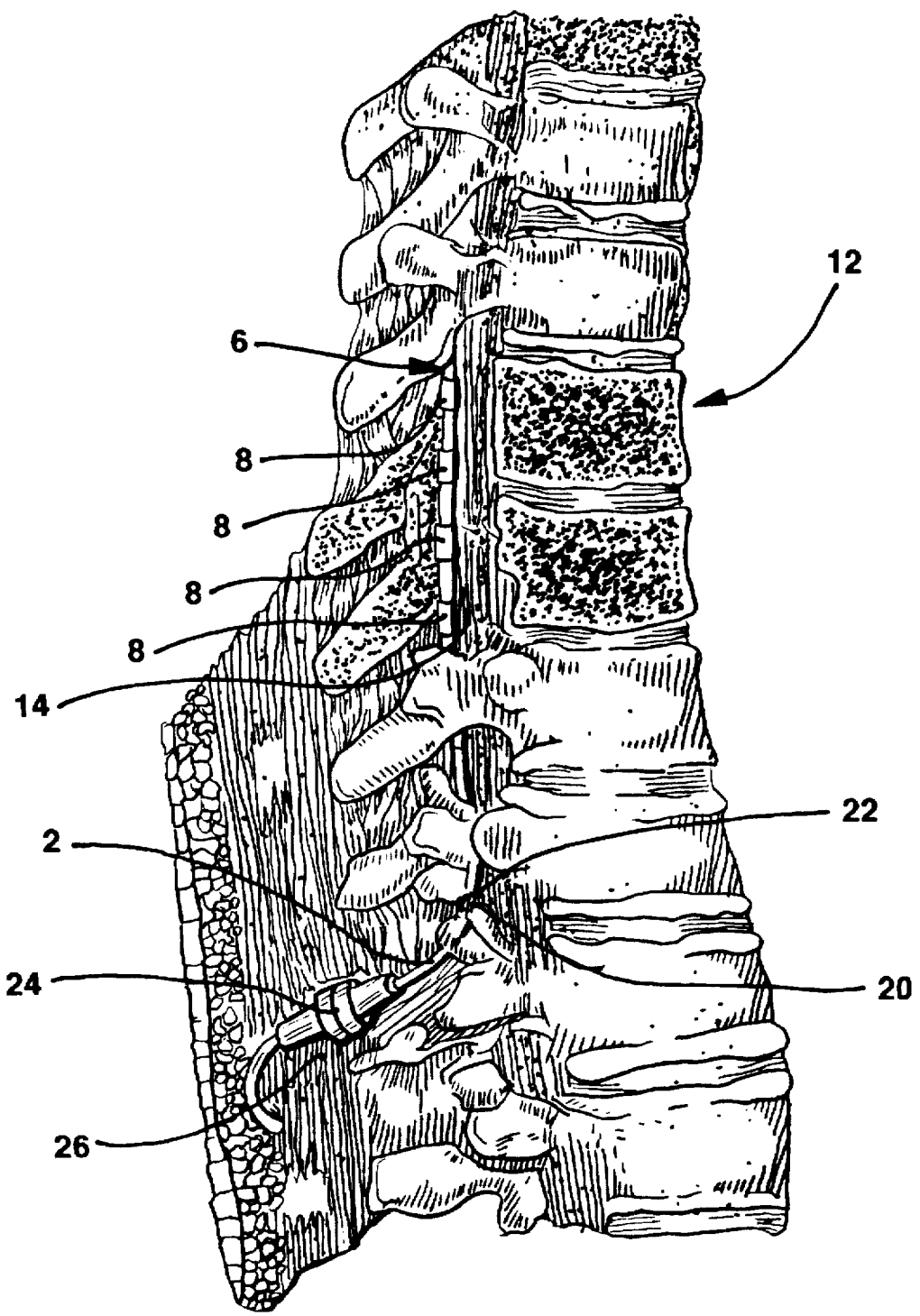
FIG. 2 is a side cross-sectional view of a spinal column showing the epidural lead of FIG. 1 in position in the epidural space.
Figure 4:
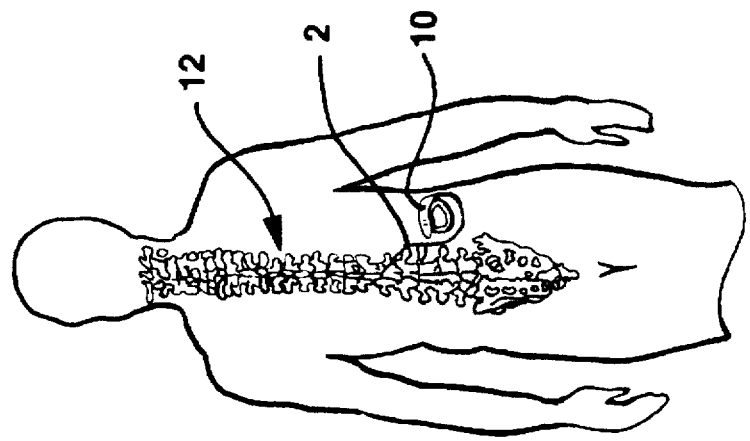
FIG. 4 is a rear view of a patient with an implanted neurological epidural lead with the patient's spinal column highlighted.
Figure 3:
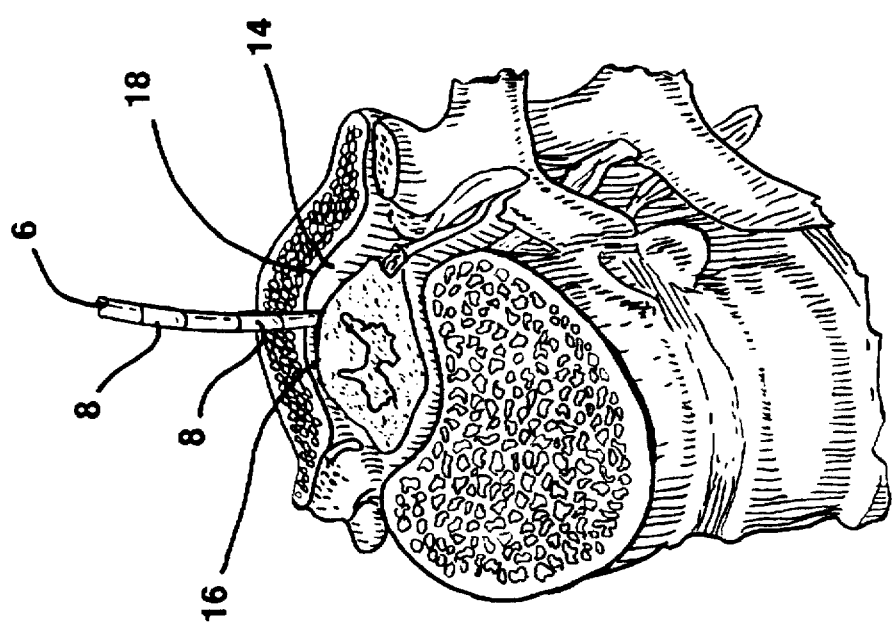
FIG. 3 is a cross-sectional view of a spinal column transverse to the view of FIG. 2 showing the epidural lead of FIG. 1 in position in the epidural space.
Figure 5:
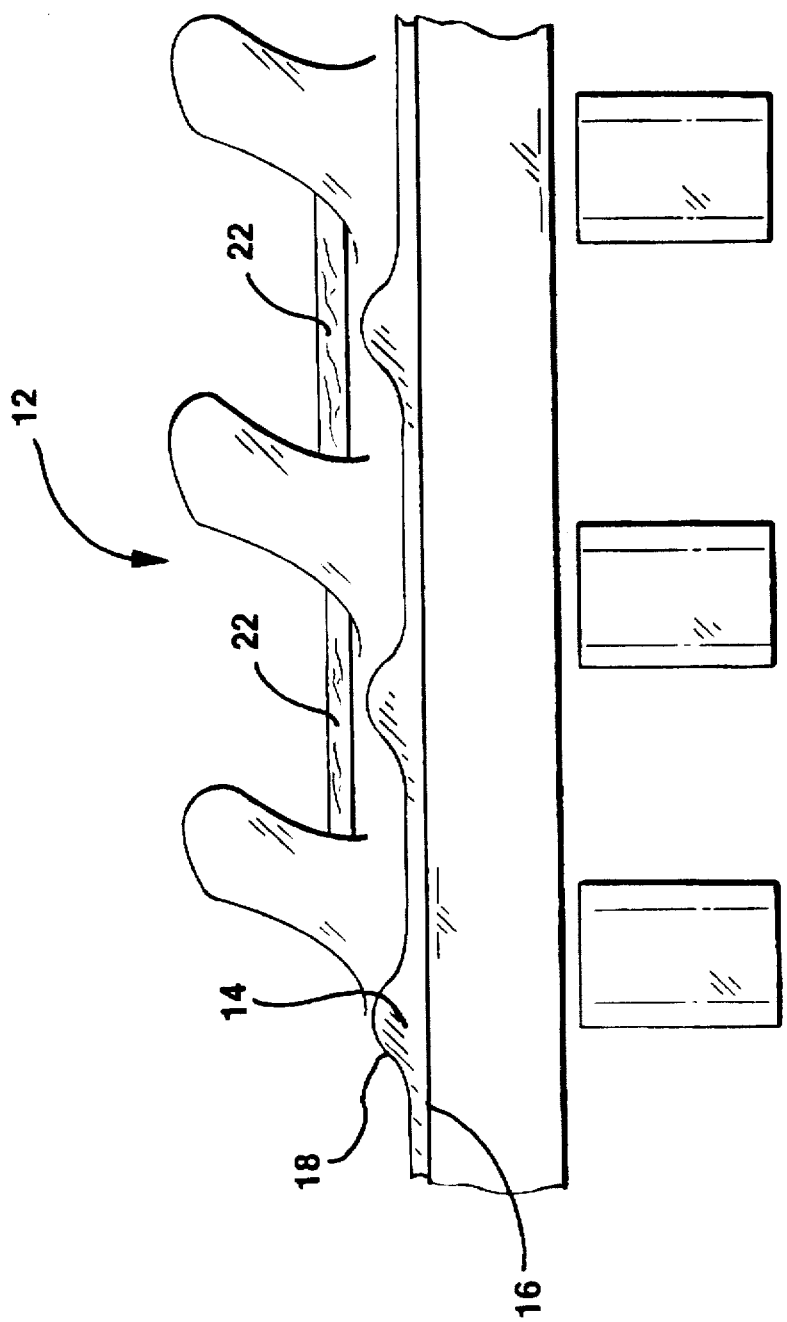
FIG. 5 is a side cross-sectional view of the spinal column with the epidural space shown.
Figure 6:
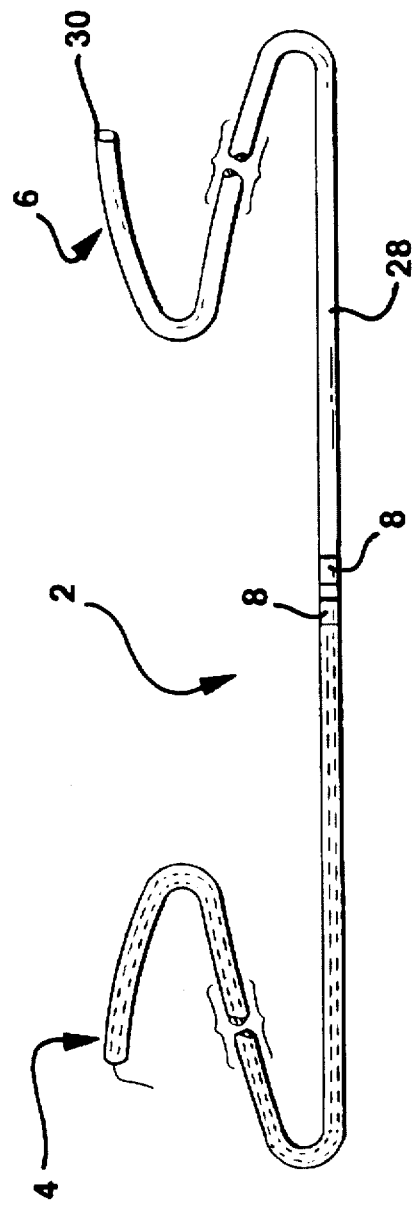
FIG. 6 is a perspective view of another prior art neurological epidural lead.
Figure 7:
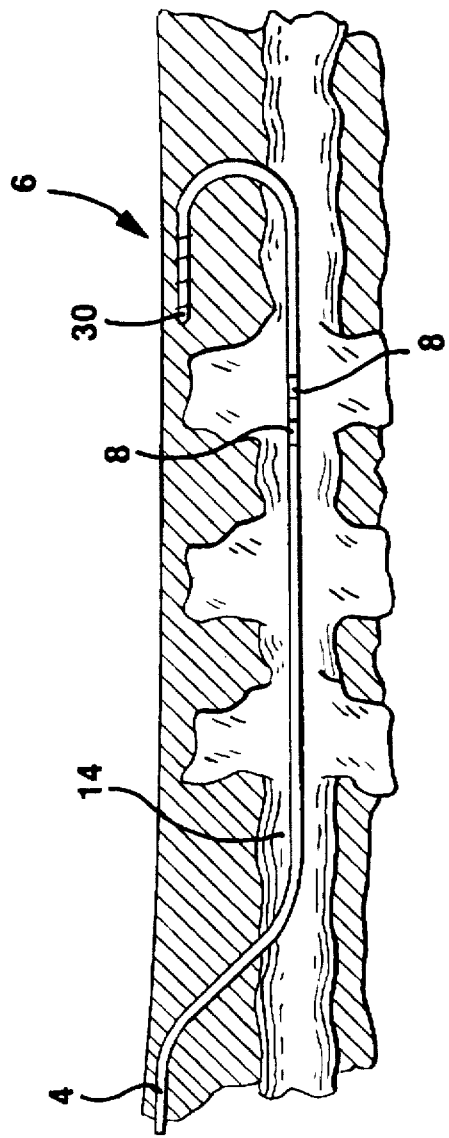
FIG. 7 is a side cross sectional view of the lead of FIG. 6 anchored in position in a patient's spinal column.

FIG. 8 shows a neurological epidural lead, generally labeled 32, made according to the invention. Lead 32 has a proximal end 34 and a distal end 36. Lead 32 has a body 38 having a series of electrodes 40 attached thereto near distal end 36. Body 38 is preferably made of an electrically non-conducting material such as polyurethane. However, body 38 may be made of any electrically non-conducting, flexible material that is inert to body tissue including, but not limited to polypropylene and silicone.

Electrodes 40 are preferably made of a conducting metal. Examples of such a conducting metal include, but are not limited to platinum and a platinum/iridium alloy. In the preferred embodiment, electrodes 40 encircle body 38. However, electrodes 40 may also have other configurations such as small pads placed along the surface of body 38. The minimum number of electrodes 40 needed for lead 32 is two. However, more electrodes 40 in addition to the minimum number of two may be added as desired. The preferred number of electrodes 40 is either four or eight. The end-to-end length of electrodes 40 in such an embodiment having four electrodes 40 is about 40 millimeters.

Electrodes 40 are spaced from each other by portions of body 38 so that there is an electrically insulating space between each of the electrodes 40. Electrodes 40 are connected to wires passing through the interior of body 38 to a connector 42 at the proximal end of lead 32. Connector 42 is attached to an implantable pulse generator (IPG) 10 such as a Itrel® IPG sold by Medtronic, Inc. of Minneapolis, Minn.

An extension 44 extends distally beyond the most distal electrode 40 and becomes the distal end 36 of lead 32. Extension 44 is preferably made of the same material as body 38. Within extension 44, there are no wires attached to electrodes 40. However, in one embodiment, a stiffening member 46 is added to extension 44 to add rigidity to extension 44. In this preferred embodiment, stiffening member 46 is preferably a polymeric or metallic material having a stiffness greater than a corresponding volume of the material of the rest of body 38.

Extension 44 has a length sufficient to ensure that extension 44 will pass through at least one part of the epidural space 14 where the dura 16 and the spinal canal wall 18 come into contact with each other. In most adults, this length will be approximately 15 to 30 millimeters in length. However, in children, this length would be smaller. In the preferred embodiment for pediatric use, the length of extension 44 is preferably about 9 to 45 millimeters in length.

In the preferred embodiment, the extension 44 will pass through at least two places in the epidural space 14 where the dura 16 comes in contact with the spinal canal wall 18. In some applications, it may be desired for extension 44 to pass through three or more such spaces. Therefore, the length of extension 44 may be as much as 90 millimeters.

In use, lead 32 is introduced percutaneously to the epidural space by inserting lead 32 into a needle which is in turn inserted into the spinal column 12 through the spinal canal wall 18. As the needle passes into epidural space 14, the needle, with lead 32 inside, will puncture the ligamentum flavum 22 and produce a small opening 20 through which body 38 will ultimately pass. Once the needle is in epidural space 14, lead 32 is pushed through the needle upward in epidural space 14 until electrodes 40 are in the desired location.

Figure 9:
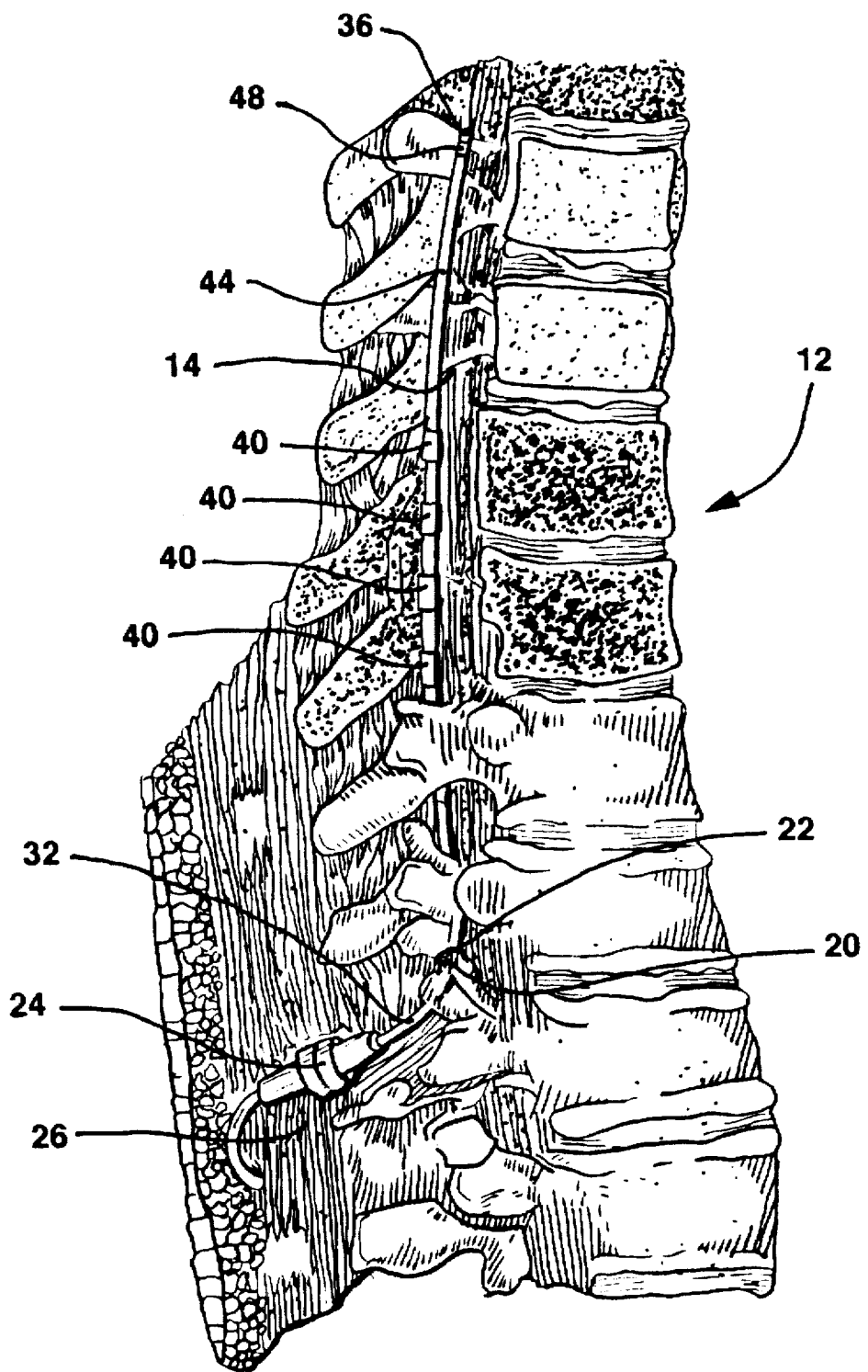
FIG. 9 is a side cross-sectional view of a spinal column with the lead of FIG. 8 in position in the epidural space.

Since extension 44 is the distal end 36 of lead 32, extension 44 will exit the needle and enter the epidural space 14 before the rest of lead 32. As extension 44 exits the needle, extension 44 moves upward in the epidural space 14. Extension 44 will pass through a series of locations in the epidural space 14 where the dura 16 and spinal canal wall 18 are in contact and also a series of locations where the dura 16 and spinal canal wall 18 are separated from each other as described above. When electrodes 40 are in the desired location in epidural space 14, the needle is removed leaving lead 32 in place within epidural space 14 (FIG. 9).

Thereafter, a stop 24 is attached to body 38 and sutured to the tissue 26 outside the spinal column 12. Stop 24 prevents lead 32 from migrating axially. Connector 42 is attached to the IPG 10 by means well known in the art. With lead 32 in the desired position in epidural space 14, contact between the dura 16 and the spinal canal wall 18 along extension 44 holds the distal end 36 of lead 32 in position in the epidural space 14 and prevents lateral movement of distal end 36. Because distal end 36 cannot move laterally, electrodes 40 cannot move laterally. Contact between body 38 and hole 20 formed in the ligamentum flavum 22 holds the portion of the body 38 within epidural space 14 that is proximal to electrodes 40 in position within the epidural space 14 and prevents lateral movement of this portion of lead 32. Consequently, lead 32 is "anchored" on both sides of electrodes 40 so there is little chance of lead 32, and electrodes 40, migrating laterally or axially in epidural space 14.

It is also desirable to be able to detect the location of distal end 36 by radiographic means both during and after insertion of lead 32. This may be done by adding a radioopaque marker 48 near the distal tip of distal end 36. Marker is preferable a cylindrical band encircling a portion of distal end 36 and having an outer diameter equal to the diameter of distal end 36. In the preferred embodiment, marker 48 is two to four millimeters long and made of a biocompatible, inert radiopaque material. Examples of such material include, but are not limited to, platinum, tantalum and titanium.

It is believed that in most cases, contact between the dura 16 and spinal canal wall 18 will provide sufficient pressure on extension 44 to hold extension 44, and consequently electrodes 40, in place. However, means may be added to extension 44 to enhance extension 44's ability to be retained in place within epidural space 14. For example, the protruding "anchoring" structure disclosed in U.S. Pat. No. 5,344,439, described above, could be added to extension 44. Further, texturing in the form of dimples, ridges, grooves or other friction producing surfaces may be added to extension 44 to enhance the frictional contact between extension 44 and the dura 16 and spinal canal wall 18.

The invention has been shown and described in connection with a specific embodiment. It is to be realized, however, that the description given herein is for the purpose of illustrating the invention and is not intended to be limiting. It is further understood that improvements and modifications to the disclosure made herein will occur to those skilled in the art and that such improvements and modifications will still fall within the scope of the invention.

What is claimed is:

1. A neurological epidural lead having a proximal end and a distal end, the lead comprising:

a body having at least two electrodes attached thereto near the distal end of the lead;

a connector attached at the proximal end of the lead;

wires connecting the electrodes to the connector;

an extension extending distally beyond the most distal electrode, the extension adapted to remain entirely within the epidural space of a spinal column, wherein the length of the extension corresponds to the length of at least one vertebral segment.

2. A lead according to claim 1 wherein the body is made of an electrically non-conducting material.

3. A lead according to claim 2 wherein the electrically non-conducting material is selected from a group consisting of polyurethane, polypropylene and silicone.

4. A lead according to claim 1 wherein the body is made of a material that is inert to body tissue.

5. A lead according to claim 1 wherein the electrodes are made of a conducting metal.

6. A lead according to claim 1 wherein the electrodes encircle the body.

7. A lead according to claim 1 wherein the number of electrodes is four.

8. A lead according to claim 1 wherein the number of electrodes is eight.

9. A lead according to claim 1 wherein the length from the most proximal electrode to the most distal electrode is about 30 millimeters.

10. A lead according to claim 1 wherein the electrodes are spaced from each other by portions of the body so that there is an electrically insulating space between each of the electrodes.

11. A lead according to claim 1 wherein the wires pass through the interior of the body.

12. A lead according to claim 1 wherein the extension is made of the same material as the body.

13. A lead according to claim 1 further comprising a stiffening member attached to the extension to add rigidity to the extension.

14. A lead according to claim 13 wherein the stiffening member is enclosed within the extension.

15. A lead according to claim 13 wherein the stiffening member is made of a material chosen from the group consisting of polymeric material and metallic material having a stiffness greater than a corresponding volume of material that the body is made of.

16. A lead according to claim 1 wherein the length of the extension is approximately 9 to 90 millimeters in length.

17. A lead according to claim 16 wherein the length of the extension is approximately 15 to 30 millimeters in length.

18. A lead according to claim 1 wherein the length of the extension is approximately 9 to 45 millimeters in length.

19. A lead according to claim 1 wherein the extension includes means for enhancing the extensions ability to be retained within the epidural space.

20. A lead according to claim 19 wherein the means for enhancing the extensions ability to be retained within the epidural space include texturing the outer surface of the extension to enhance the frictional contact between the extension and the dura and spinal canal wall.

21. A lead according to claim 20 wherein the texturing added to the outer surface of the extension includes texturing chosen from the group consisting of dimples, ridges and grooves.

22. A lead according to claim 19 wherein the means for enhancing the extensions ability to be retained within the epidural space includes adding protrusions to the outer surface of the extension to enhance the frictional contact between the extension and the dura and spinal canal wall.

23. A system for producing parasthesia in a patient comprising:

a neurological epidural lead having a proximal end and a distal end, the lead comprising:

a body having at least two electrodes attached thereto near the distal end of the lead;

a connector attached at the proximal end of the lead;

wires connecting the electrodes to the connector;

an extension extending distally beyond the most distal electrode, the extension adapted to remain entirely in the epidural space of a spinal column, wherein the length of the extension corresponds to the length of at least one vertebral segment; and an implantable electrical pulse generator electrically connected to the wires.

24. A method for anchoring a neurological epidural lead in the epidural space of a patient, the method comprising the steps of:

providing a lead having a proximal end and a distal end, the lead having a body with at least two electrodes attached thereto near the distal end of the lead, a connector attached at the proximal end of the lead, wires connecting the electrodes to the connector and an extension extending distally beyond the most distal electrode for a distance corresponding to the length of at least one vertebral segment, the extension adapted to remain entirely in the epidural space of a spinal column;

inserting the lead into a needle having a proximal and a patient contacting distal end, the extension being coterminous with the distal end of the needle;

inserting the needle into a spinal column through a spinal canal wall;

puncturing the ligamentum flavum with the needle to produce a small opening into the epidural space;

pushing the lead out of the needle upward in the epidural space until the electrodes are in the desired location and the extension passes through at least one location in the epidural space where the dura and the spinal canal wall are in contact and wherein the distal end of the lead is retained entirely within the epidural space;

removing the needle;

whereby contact between the extension and the dura and spinal canal wall hold the extension in a fixed relation within the epidural space.

25. The method of claim 24 further comprising the step of anchoring the proximal end of the lead outside the spinal column to prevent axial movement of the lead.

26. A method according to claim 24 wherein the step of providing a lead includes the step of providing a lead having means for enhancing the extension's ability to be retained within the epidural space.

27. A neurological epidural lead having a proximal end and a distal end, the lead comprising:

a body having at least two electrodes attached thereto near the distal end of the lead;

a connector attached at the proximal end of the lead;

wires connecting the electrodes to the connector;

an extension extending distally beyond the most distal electrode, the extension adapted to remain entirely within the epidural space of a spinal column, wherein the length of the extension is approximately 9 to 90 millimeters in length.

28. A lead according to claim 27 wherein the length of the extension is approximately 15 to 30 millimeters in length.

29. A lead according to claim 27 wherein the length of the extension is approximately 9 to 45 millimeters in length.

30. A lead according to claim 27 wherein the extension includes means for enhancing the extensions ability to be retained within the epidural space.

31. A method for anchoring a neurological epidural lead in the epidural space of a patient, the method comprising the steps of:

providing a lead having a proximal end and a distal end, the lead having a body with at least two electrodes attached thereto near the distal end of the lead, a connector attached at the proximal end of the lead, wires connecting the electrodes to the connector and an extension extending distally beyond the most distal electrode for a distance of approximately 9 to 90 millimeters, the extension adapted to remain entirely in the epidural space of a spinal column;

inserting the lead into a needle having a proximal and a patient contacting distal end, the extension being coterminous with the distal end of the needle;

inserting the needle into a spinal column through a spinal canal wall;

puncturing the ligamentum flavum with the needle to produce a small opening into the epidural space;

pushing the lead out of the needle upward in the epidural space until the electrodes are in the desired location and the extension passes through at least one location in the epidural space where the dura and the spinal canal wall are in contact and wherein the distal end of the lead is retained entirely within the epidural space;

removing the needle;

whereby contact between the extension and the dura and spinal canal wall hold the extension in a fixed relation within the epidural space.

32. A method according to claim 31 wherein the step of providing a lead includes the step of providing a lead having means for enhancing the extension's ability to be retained within the epidural space.

* * * * *